United States Patent [19]

Graefe et al.

[11] Patent Number: 4,958,041

[45] Date of Patent: Sep. 18, 1990

[54] METHODS FOR PRODUCING DIORGANODIALKOXYSILANES

[75] Inventors: Jurgen Graefe, Selm-Cappenberg; Wolfram Uzick, Dortmund; Udo Weinberg, Bergkamen, all of Fed. Rep. of Germany

[73] Assignee: Schering Aktiengesellschaft, Bergkamen, Fed. Rep. of Germany

[21] Appl. No.: 371,397

[22] Filed: Jun. 26, 1989

[30] Foreign Application Priority Data

Jun. 25, 1988 [DE] Fed. Rep. of Germany ....... 3821483

[51] Int. Cl.$^5$ .............................................. C07F 7/18
[52] U.S. Cl. ................................................... 556/480
[58] Field of Search ........................................ 556/480

[56] References Cited

U.S. PATENT DOCUMENTS

| | | | |
|---|---|---|---|
| 2,380,057 | 7/1945 | McGregor et al. | 556/480 |
| 2,414,505 | 1/1947 | Arntzen | 556/480 |
| 2,671,101 | 3/1954 | Frische et al. | 556/480 |
| 2,671,795 | 3/1954 | Frishe et al. | 556/480 |
| 2,709,692 | 5/1955 | Gainer | 556/480 X |
| 4,748,262 | 5/1988 | Ishihara et al. | 556/480 |
| 4,777,278 | 10/1988 | Band et al. | 556/480 |

Primary Examiner—Paul F. Shaver
Attorney, Agent, or Firm—Scully, Scott, Murphy & Presser

[57] ABSTRACT

In a method for the selective production of diorganodialkoxysilanes of the general formula

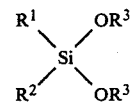

by reaction of tetraalkoxysilanes of the formula Si(OR$^3$)$_4$ and monoorganotrialkoxysilanes of the formula R$^1$Si(OR$^3$)$_3$ respectively with Grignard reagents, the desired reaction products are produced in high yield and without undesirable by-products and in high yield.

28 Claims, No Drawings

METHODS FOR PRODUCING DIORGANODIALKOXYSILANES

FIELD OF THE INVENTION

This invention provides a method of selective production of diorganodialkoxysilanes by reaction of tetraalkoxysilanes or monoorganotrialkoxysilanes with a Grignard reagent.

BACKGROUND OF THE INVENTION

Disubstituted dialkoxysilanes having the general structure $R_2Si(OR)_2$ are included, among other things, as stereomodifiers in catalysts for the production of polypropylenes (PP) (European Patent Application EP-A-No. 0,231,878). Particularly advantageous for that use are disubstituted dialkoxysilanes having the formula $R^1R^2Si(OR^3)_2$, and especially those compounds where $R^1$ and $R^2$ are branched alkyl chains (EP-A-No. 0,250,229 and DE-A-No. 36 29 932).

It is well known that disubstituted dialkoxysilanes $R^aR^bSi(OR^c)_2$ can be produced through alkylation or arylation of tetraalkoxysilanes and only occasionally produced by reaction of monosubstituted trialkoxysilanes with Grignard reagents (Houben-Weyl, Methods of Organic Chemistry, XIII/5, 180 p).

However, as a rule, the reaction products are produced as mixtures of diorganodialkoxysilanes with monoorganotrialkoxysilanes and/or triorganomonoalkoxysilanes, so that the isolation of the desired diorganodialkoxysilane requires a separation step. Hence, one must accept a relatively low product yield with a concomitant increase in production costs (Z. Lasocki, Bull. Acad. Polon. Sci., Ser. Sci. Chim. 12 (5), 281–287 (1964)).

It has now surprisingly been found that by reacting monoorganotrialkoxysilanes $R^1Si(OR^3)_3$ or tetraalkoxysilanes $Si(OR^3)_4$ with Grignard reagents $R^2MgX$ in appropriate solvents certain diorganodialkoxysilanes $R^1R^2Si(OR^3)_2$, depending on the structure of the $R^1$ and $R^2$ groups, are readily produced with a high degree of selectivity and in high yields. The high selectivity and yield obtained by the methods of the present invention provides a means to rapidly and cost efficiently produce diorganodialkoxysilanes. Selective production of diorganodialkoxysilanes depends on at least one of $R^1$ and $R^2$, and preferably both, being a branched or a cyclic alkyl group. This dependence was heretofore unknown to the skilled artisan.

SUMMARY OF THE INVENTION

The present invention provides a method of selective production of diorganodialkoxysilanes by reaction of tetraalkoxysilanes or monoorganotrialkoxysilanes with a Grignard reagent.

DETAILED DESCRIPTION

This invention thus provides a method of selective production of diorganodialkoxysilanes having the general formula

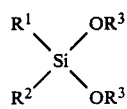

by the reaction of tetraalkoxysilanes having the formula $Si(OR^3)_4$ or monoorganotrialkoxysilanes having the general formula $R^1Si(OR^3)_3$ with an alkylating-effective amount of a Grignard reagent having the formula $R^2MgX$ where X is Cl, Br, I, and the R groups have the following meanings:

$R^1$ and $R^2$ are independently an alkyl group or a cycloalkyl group having 3 to 10 carbon atoms, wherein at least one of $R^1$ and $R^2$ is a branched alkyl group having the branched alkyl group at a secondary carbon in the α- or β-position to the Si;

$R^1$ is $R^2$ when reacting a tetraalkoxysilane with the Grignard reagent;

each $R^3$ may be the same or different and is an alkyl group having 1 to 5 carbon atoms.

An embodiment of $R^1$ and $R^2$ is represented by the formula

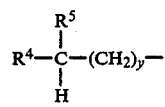

wherein
y is 1 or 0;
$R^4$ is alkyl having 1 to 7 carbon atoms;
$R^5$ is alkyl having 1 to 7 carbon atoms; or
$R^4$ and $R^5$ taken together with the carbon atom to which they are attached form a cycloalkyl group having 3 to 10 carbon atoms.

Preferably $R^1$ and $R^2$ are branched alkyl groups having 3 to 6 carbon atoms and cycloalkyl groups having 5 to 7 carbon atoms and $R^3$ is a methyl or ethyl group.

The diorganodialkoxysilane can be formed from the tetraalkoxysilane in one step by reacting the latter with $R^2MgX$ in accordance with the procedure described herein. In this case, the product

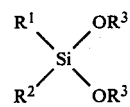

is formed, wherein $R^1$, $R^2$ and $R^3$ are as defined hereinabove and $R^1$ is the same as $R^2$.

Another embodiment of the present invention provides a process for preparing a diorganodialkoxysilane having the formula

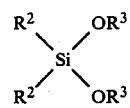

by reacting a tetraalkoxysilane of the formula $Si(OR^3)_4$ with an alkylating agent, wherein the alkylating agent is a Grignard reagent having a secondary carbon atom of the formula $R^2MgX$, wherein $R^2$ is

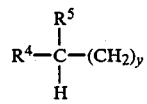

$R^4$ is alkyl having 1 to 7 carbon atoms,
$R^5$ is alkyl having 1 to 7 carbon atoms, or R⁴ and R⁵ taken together form a cycloalkyl group having 3 to 10 carbon atoms, each R³ is the same or different and is alkyl having 1 to 5 carbon atoms, and X is Cl, Br and I, and y is 0 or 1.

The reaction of an alkylating-effective amount of the Grignard reagent with the tetralkoxysilane forms a substantially pure diorganodialkoxysilane in quantitative yields.

A further embodiment of the present invention provides a process for preparing a diorganodialkoxysilane having the formula

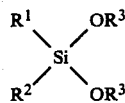

by reacting an alkylating agent with a monoorganotrialkoxysilane, wherein the monoorganotrialkoxysilane has a secondary carbon atom or the alkylating agent has a secondary carbon atom, and wherein the monoorganotrialkoxysilane has the formula R¹Si(OR³)₃ and the Grignard reagent has the formula R²MgX, and one of R¹ and R² is

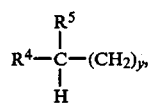

and the other is n-alkyl having 3 to 10 carbon atoms or is

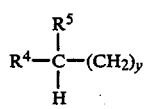

R⁴ is alkyl having 1 to 7 carbon atoms,

R⁵ is alkyl having 1 to 7 carbon atoms, or

R⁴ and R⁵ taken together with the carbon atom to which they are attached form a cycloalkyl group having 3 to 10 carbon atoms, each R³ may be the same or different and is alkyl having 1 to 5 carbon atoms, X is Br, Cl or I, and y is 0 or 1.

The reaction of an alkylating-effective amount of the Grignard reagent with the monoorganotrialkoxysilane forms a substantially pure diorganodialkoxysilane in quantitative yields.

When using a slight excess of the Grignard reagent R²MgX, the monoorganotrialkoxysilane R¹Si(OR³)₃ or tetraalkoxysilane Si(OR³)₄ is nearly quantitatively converted into the diorganodialkoxysilane R¹R²Si(OR³)₂ without observing the production of triorganomonoalkoxysilanes by further alkylation.

The reaction is preferably carried out at a temperature from about 0° to about 90° C.

Suitable solvents include dialkyl ethers that, because of their physical properties, are useful in the above-named temperature ranges.

The boiling point of the solvent should, on one hand, not be too low and should also be in a range that will be compatible with the reaction temperature. On the other hand, the boiling point must not be so high that solvent losses from the reaction products present difficulties. Preferred solvents for the methods of the present invention are dialkylethers such as diethylether and, especially preferred, is methyl-tert-butylether.

Those cyclic ethers typically used as solvents for Grignard reactions, such as tetrahydrofuran or 1,4-dioxan, have been found less suitable for the present invention.

In the present invention, an alkylating-effective amount of a Grignard reagent is used for producing the diorganodialkoxysilanes of the present invention. It is preferred for that same amount to be a molar ratio of tetralkoxysilane or monoorganotrialkoxysilane to Grignard reagent ranging from about 1:1 to about 1:10. When tetraalkoxysilanes are reacted with the Grignard reagent the most preferred molar ratio ranges from about 1:2 to about 1:5. When monoorganotrialkoxysilanes are reacted with a Grignard reagent the most preferred molar ratio ranges from about 1:1 to about 1:3.

The methods of the present invention provide substantially pure diorganodialkoxysilanes in high selectivity and in quantitative yields. As used herein, "substantially pure" means that very little, if any, impurities are present. In the process of the present reaction, the desired diorganodialkoxysilane is at least 90% pure, and preferably greater than 97% pure. As used herein, "quantitative yield" means that the reactants are converted to products with high selectivity. According to the process of the present invention, the product is formed in at least 90% yield and preferably at least 95% yield.

The methods of the present invention are exemplified by the reaction schemes drawn below for producing isobutylcyclohexyldimethoxysilane (R¹=iso-C₄H₉, R²=cyclo/3-C₆H₁₂, R³=CH₃) from isobutyltrimethoxysilane (R¹Si(OR³)₃ where R¹=iso-C₄H₉ and R³=CH₃) (Scheme 1) and diisopropyldimethoxysilane (R¹=R²=iso-C₃H₇, R³=CH₃) from tetramethoxysilane (R³=CH₃) (Scheme 2):

Scheme 1

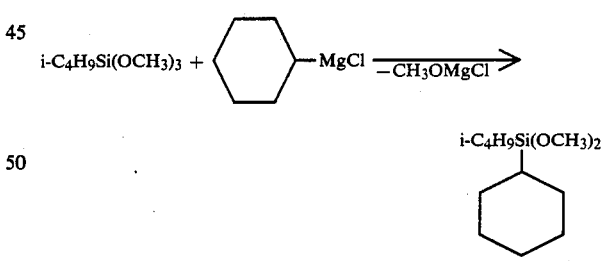

Scheme 2

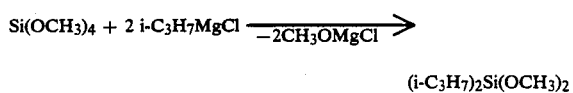

(i-C₃H₇)₂Si(OCH₃)₂

It is advantageous for working up the reaction mixture and for relatively high product purity to quench any excess Grignard reagent remaining in the reaction mixture with stochiometric amounts of an alcohol R³OH. After separation of the solid by-product R³OMgX by filtration or centrifugation, followed by evaporation of the solvent, the resulting diorganodialkoxysilane is obtained in a yield greater than 95% and a purity greater than 97%. This purity may be sufficient for the intended use of the compound and thus saves additional purification steps.

A further simplification for producing diorganodialkoxysilane results when, in accordance with known procedures (Chemical Abstracts 32: 7892, 105: 134116n, 105: 134117p) for separate production of a Grignard reagent $R^2MgX$, the monoorganotrialkoxysilane $R^1Si(OR^3)_3$ or the tetraalkoxysilane $Si(OR^3)_4$ are combined directly with metallic magnesium and an organic halide $R^2X$ in the presence of a suitable solvent.

In contrast to present technology, a high selectivity is observed which depends on the nature of the $R^1$ and $R^2$. Thus, for example by the present method, isobutylcyclohexyldimethoxysilane (cf. Scheme 1) is obtained with a yield greater than 98% and a purity greater than 97%. Likewise, diisopropyldimethoxysilane (cf. Scheme 2) is obtained with a yield greater than 98% and a purity greater than 98%.

Examples 1 to 6 and Tables 1 and 2 further illustrate the methods for producing the compounds of the present invention.

EXAMPLE 1A

Isobutylcyclohexyldimethoxysilane

Under an inert gas, 152.0 g isobutyltrimethoxy silane (0.85 mol) was dissolved in 50 ml diethylether. While stirring, 667 ml of a 1.5 molar solution of cyclohexylmagnesiumchloride in ether was added dropwise to the solution at a rate to maintain a moderate reflux. At the end of the addition, the reaction was continued under reflux for several hours. After cooling the reaction mixture, 4.8 g methanol (0.15 mol) was added, stirred for a few minutes and then the resulting precipitate was removed by filtration. The filter cake was washed with several portions of diethylether. The solvent was then evaporated from the combined filtrates using a water aspirator. The remaining residue consisted of 192.7 g (98.4% of the theoretical yield) isobutylcyclohexyldimethoxysilane, which had a purity of 98% according to gas chromatography (GC). Isobutyldicyclohexylmethoxysilane was not detected by GC.

EXAMPLE 1B

Isobutylcyclohexyldimethoxysilane

Under an inert gas, 24.3 g magnesium chips (1.0 mol) were combined with about 10 ml methyl-tert-butylether, an iodine crystal and 3.6 g cyclohexylchloride (0.03 mol). To start the reaction, a solution of 152.0 g isobutyltrimethoxysilane (0.85 mol) and 115.0 g cyclohexylchloride (0.97 mol) in 130 ml methyl-tert-butylether was added dropwise, with stirring, to the first mixture at a rate to maintain a moderate reflux. At the end of this addition, the reaction was allowed to reflux for two more hours. After cooling the reaction mixture, 4.8 g methanol (0.15 mol) was added, stirred for a few minutes and then the precipitate was removed by filtration. The filter cake was washed with several portions of methyl-tert-butylether. The solvent was evaporated from the combined filtrates by water vacuum. The remaining residue consisted of 192.5 g (98.4% of the theoretical yield) isobutylcyclohexyldimethoxysilane which had a purity of 98% according to GC. Isobutyldicyclohexylmethoxysilane was not detected by GC.

Procedures analogous to Example 1 were used to obtain the following diorganodimethoxysilanes (Examples 2-5):

EXAMPLE 2

Isobutylcyclopentyldimethoxysilane

Purity: 97%, Yield: 98% of theoretical. Isobutyldicyclopentylmethoxysilane was not detected by GC.

EXAMPLE 3

Isobutyl-sec-butyldimethoxysilane

Purity 98.5%, Yield: 98.3% of theoretical. Isobutyl-di-sec-butylmethoxysilane was not detected by GC.

EXAMPLE 4

Isobutyl-n-propyldimethoxysilane

Purity: 99%, Yield: 98.2% of theoretical. Isobutyl-di-n-propylmethoxysilane was not detected by GC.

EXAMPLE 5

Isobutylisopropyldimethoxysilane

Purity: 99%, Yield: 98.1% of theoretical. Isobutyl-diisopropylmethoxysilane was not detected by GC.

As the following Example 6 shows, the alkylation of tetraalkoxysilanes to form dialkyldialkoxysilanes can occur with an equally high selectivity.

EXAMPLE 6

Diisopropyldimethoxysilane

Under an inert gas, 24.2 g magnesium chips (1.0 mol) were combined with about 20 ml methyl-tert-butylether, an iodine crystal and 3.1 g 2-chloropropane (0.04 mol). To start the reaction a solution of 61.9 g tetramethoxysilane (0.41 mol) and 75.4 g 2-chloropropane (0.96 mol) in 140 ml methyl-tert-butylether was added dropwise, with stirring, to the first mixture at a rate to maintain a moderate reflux. After addition of the solution, the reaction was allowed to reflux for six more hours. After cooling the reaction mixture, 6.0 g methanol (0.19 mol) was added, the mixture was stirred for a few minutes and then the resulting precipitate was removed by filtration. After washing the filter cake with several portions of methyl-tert-butylether, the solvent was distilled from the combined filtrates. The remaining residue consisted of 70.5 g diisopropyldimethoxysilane (98% of the theoretical yield) which had a purity of 98% according to GC. Triisopropylmethoxysilane was not detected by GC.

TABLE 1

Synthesis of diorganodialkoxysilanes from monoorganotrialkoxysilanes[a,b]

| Reactant | Grignard Reagent | Product | Yield (%) (by GC) |
|---|---|---|---|
| secBuSi(OMe)$_3$ | iBuMgCl | secBu-iBuSi(OMe)$_2$ | 98 |
| iBuSi(OMe)$_3$ | nPropMgCl | iBu-nPropSi(OMe)$_2$ | 99 |
| " | iPropMgCl | iBu-iPropSi(OMe)$_2$ | 99 |
| " | cPentMgBr | iBu-cPentSi(OMe)$_2$ | 97 |
| " | cHexMgCl | iBu-cHexSi(OMe)$_2$ | 98 |
| nOcSi(OEt)$_3$ | secBuMgCl | nOc-secBuSi(OEt)$_2$ | 97 |
| iPropSi(OProp)$_3$ | cPentMgCl | iProp-cPentSi(OProp)$_2$ | 98 |

[a]Abbreviations - see Table 3.
[b]Prepared in accordance with Examples 1-5 or in analogy to Example 1.

TABLE 2

Synthesis of diorganodialkoxysilanes from tetraalkoxysilanes[a,b]

| Reactant | Grignard Reagent | Product | Yield (%) (by GC) |
|---|---|---|---|
| Si(OMe)$_4$ | iPropMgCl | (iProp)$_2$Si(OMe)$_2$ | 98 |
| " | cPentMgBr | cPent$_2$Si(OMe)$_2$ | 97 |
| Si(OProp)$_4$ | iAmMgBr | iAm$_2$Si(OProp)$_2$ | 96 |
| Si(OProp)$_4$ | secBuMgCl | secBu$_2$Si(OProp)$_2$ | 98 |
| Si(OPent)$_4$ | secBuMgCl | secBu$_2$Si(OPent)$_2$ | 97 |

[a]Abbreviations - see Table 3.
[b]Prepared in analogy to Example 6.

Comparative Example 1 indicates that, using the methods of the present invention, it is possible to make diorganodialkoxysilanes $R^1R^2Si(OR^3)_2$ with high selectivity, when the reaction of monoorganotrialkoxysilane $R^1Si(OR^3)_3$ is conducted with a considerable excess of the in situ-produced Grignard reagent $R^2MgX$. Indeed, by suitable choice of $R^1$ and $R^2$ groups, the formation of triorganomonoalkoxysilanes $R^1R^2_2SiOR^3$ are not observed under these conditions.

COMPARATIVE EXAMPLE 1

Attempted preparation of isobutyldiisopropylmethoxysilane

In analogy to Example 1, 8.2 g magnesium chips (0.338 mol) were combined with 26.5 g 2-chloropropane (0.338 mol and 30.0 g isobutyltrimethoxysilane (0.169 mol) in 80 ml methyl-tert-butylether. .

The final product was isobutylisopropyldimethoxysilane. Isobutyldiisopropylmethoxysilane was not detected by GC.

As shown by the comparative examples listed in Table 3, the reaction of monoorganotrialkoxysilanes $R^1Si(OR^3)_3$ with tert-butylmagnesiumbromide ($R^2$=t-butyl) does not lead to the formation of the corresponding diorganodialkoxysilanes $R^1R^2Si(OR^3)_2$. Furthermore, it is apparent from the other examples that the formation of alkylaryldialkoxysilanes from monoalkyltrialkoxysilanes $R^1Si(OR^3)_3$ and arylmagnesium halides $R^2MgX$ proceeds with a comparatively less selectivity. Nevertheless, the main product consists of diorganodialkoxysilane $R^1R^2Si(OR^3)_2$ in these reactions. The same result also occurs for the production of di-n-alkyldialkoxysilanes and diaryldialkoxysilanes from tetraalkoxysilanes.

TABLE 3

Comparative Examples[a,b]

| Reactant | Grignard Reagent | Product | Yield (%) (by GC) |
|---|---|---|---|
| iBuSi(OMe)$_3$ | tBuMgCl | — | no reaction |
| iBuSi(OMe)$_3$ | PhMgBr | iBuPhSi(OMe)$_2$ | 71 |
| | | iBuPh$_2$Si(OMe) | 13 |
| iBuSi(OMe)$_3$ | pTolMgBr | iBu(pTol)Si(OMe)$_2$ | 50 |
| | | iBu(pTol)$_2$Si(OMe) | 12 |
| Si(OMe)$_4$ | nHexMgBr | nHexSi(OMe)$_3$ | 13 |
| | | nHex$_2$Si(OMe)$_2$ | 77 |
| | | nHex$_3$Si(OMe) | 10 |
| Si(OMe)$_4$ | pTolMgBr | pTolSi(OMe)$_3$ | 7 |
| | | pTol$_2$Si(OMe)$_2$ | 82 |
| | | pTol$_3$Si(OMe) | 4 |

[a]Abbreviations:
Me = methyl, Et = ethyl, Prop = propyl, Am = amyl, Pent = pentyl, pTol = para-tolyl, Ph = phenyl, Oc = octyl; n = normal, i = iso, sec = secondary, t = tertiary, c = cyclo.
[b]Prepared in analogy to Comparative Example 1.

We claim:

1. A method of selective production of diorganodialkoxysilane having the general formula:

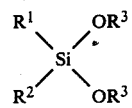

which comprises reacting at a temperature of about 0° to about 90° C. a tetraalkoxysilane having the formula Si(OR$^3$)$_4$ or a monoorganotrialkoxysilanes having the formula R$^1$Si(OR$^3$)$_3$ with an alkylating effective amount of a Grignard reagent having the formula R$^2$MgX, wherein X is Br, Cl or I;
R$^1$ and R$^2$ are independently an alkyl group or a cycloalkyl group having 3 to 10 carbon atoms, wherein at least one of R$^1$ and R$^2$ is a branched alkyl group having the branched alkyl group at the α- or β- carbon to the Si;
R$^1$ is R$^2$ when reacting the tetraalkoxysilane with the Grignard reagent; and.
each R$^3$ may be the same or different and is an alkyl group having 1 to 5 carbon atoms.

2. The method according to claim 1 wherein R$^1$ or R$^2$ is

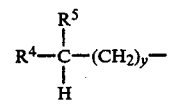

wherein
y is 1 or 0;
R$^4$ is alkyl having 1 to 7 carbon atoms;
R$^5$ is alkyl having 1 to 7 carbon atoms; or
R$^4$ and R$^5$ taken together with the carbon atom to which they are attached form a cycloalkyl group having 3 to 10 carbon atoms.

3. The method of selective production of dialkyldialkoxysilanes according to claim 1 wherein R$^1$ and R$^2$ are branched alkyl groups having 3 to 6 carbon atoms.

4. The method of selective production of dicycloalkyldialkoxysilanes according to claim 1, wherein R$^1$ and R$^2$ are cycloalkyl groups having 5 to 7 carbon atoms.

5. The method of selective production of alkylcycloalkyldialkoxysilanes according to claim 1, wherein R$^1$ is a branched alkyl group having 3 to 6 carbon atoms and R$^2$ is a cycloalkyl group having 5 to 7 carbon atoms.

6. The method of selective production of diorganodialkoxysilanes according to any one of claims 1 to 5, wherein R$^3$ is a methyl or ethyl group.

7. The method according to any one of claims 1 to 5, wherein the Grignard reagent (R$^2$MgX) is formed in situ.

8. The method according to any one of claims 1 to 5, wherein X is Cl or Br.

9. The method of claim 1, wherein the reaction is conducted in methyl-tert-butylether.

10. The method of claim 1 which comprises quenching any excess Grignard reagent remaining after reaction with a stoichiometric amount of an alcohol R$^3$OH thereby forming a side product R$^3$OMgX.

11. The method of claim 1 wherein the effective amount of the Grignard reagent is present in a molar ratio of tetraalkoxysilane to Grignard reagent ranging from 1:2 to 1:10.

12. The method of claim 11 wherein the molar ratio range is from 1:2 to 1:5.

13. The method of claim 1 wherein the effective amount of the Grignard reagent is present in a molar ratio of monoorganotrialkoxysilane to Grignard reagent ranging from 1:1 to 1:10.

14. The method of claim 13 wherein the molar ratio ranges from 1:1 to 1:3.

15. The method of claim 1 wherein the monoorganotrialkoxysilane is sec-butyltrimethoxysilane, the Grignard reagent is isobutylmagnesium chloride and the product is isobutyl-sec-butyldimethoxysilane; the monoorganotrialkoxysilane is isobutyltrmethoxysilane, the Grignard reagent is n-propylmagnesium chloride and the product is isobutyy-n-propyltrimethoxysilane; the monoorganotrialkoxysilane is isobutyltrimethoxysilane, the Grignard reagent is isopropylmagnesium chloride and the product is isobutylisopropyldimethoxysilane; the monoorganotrialkoxysilane is isobutyltrimethoxysilane, the Grignard reagent is cyclopentylmagnesium chloride and the product is isobutylcyclopentyldimethoxysilane; the monoorganotrialkoxysilane is isobutyltrimethoxysilane, the Grignard reagent is cyclohexylmagnesium chloride and the product is isobutylcyclohexyldimethoxysilane; the monoorganotrialkoxysilane is n-octyltriethoxysilane, the Grignard reagent is sec-butylmagnesium chloride and the product is n-octyl-secbutyldiethoxysilane or the monoorganotrialkoxysilane is isopropyltripropoxysilane, the Grignard reagent is cyclopentylmagnesium chloride and the product is isopropylcyclopentyldipropoxysilane.

16. The method of claim 1 wherein the tetraalkoxysilane is tetramethoxysilane, the Grignard reagent is isopropylmagnesium chloride and the product is diisopropyldimethoxysilane; the tetraalkoxysilane is tetramethoxysilane, the Grignard reagent is cyclopentylmagnesium chloride and the product is dicyclopentyldimethoxysilane; the tetraalkoxysilane is tetramethoxysilane, the Grignard reagent is isoamylmagnesium chloride and the product is diisoamyldimethoxysilane; the tetraalkoxysilane is tetrapropoxysilane, the Grignard reagent is sec-butylmagnesium chloride and the product is di-sec-butyldipropoxysilane or the tetraalkoxysilane is tetrapentoxysilane, the Grignard reagent is sec-butylmagnesium chloride and the product is di-sec-butyldipentoxysilane.

17. In a process for preparing a diorganodialkoxysilane having the formula

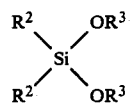

by reacting a tetraalkoxysilane of the formula Si(OR$^3$)$_4$ with an alkylating agent, the improvement comprises selecting as the alkylating agent a Grignard reagent having a secondary carbon atom, of the formula R$^2$MgX wherein
R$^2$ is

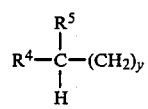

R$^4$ is alkyl having 1 to 7 carbon atoms,

R$^5$ is alkyl having 1 to 7 carbon atoms, or
R$^4$ and R$^5$ taken together form a cycloalkyl group having 3 to 10 carbon atoms,
each R$^3$ is the same or different and is alkyl having 1 to 5 carbon atoms, and
X is Cl, Br and I, and
y=0 or 1,
reacting an alkylating-effective amount of said Grignard reagent with said tetraalkoxysilane and thereby forming a substantially pure diorganodialkoxysilane in quantitative yields.

18. The improved process of claim 17 wherein the yield is greater than 95% and purity greater than 97%.

19. The improved process according to claim 17 wherein the effective amount of Grignard reagent is present in a molar ratio of tetraalkoxysilane to Grignard reagent ranging from 1:2 to 1:10.

20. The improved process according to claim 19 wherein the molar ratio range from 1:2 to 1:5.

21. The improved process of claim 17, wherein the reaction is conducted in methyl-tert-butylether.

22. The improved process of claim 17 which comprises quenching any excess Grignard reagent remaining after reaction with a stoichiometric amount of an alcohol R$^3$OH thereby forming a side product R$^3$OMgX.

23. In a process for preparing a diorganodialkoxysilane having the formula

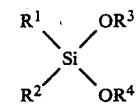

by reacting an alkylating agent with a monoorganotrialkoxysilane, the improvement which comprises selecting a monoorganotrialkoxysilane having a secondary carbon atom or an alkylating agent having a secondary carbon atom, wherein the monoorganotrialkoxysilane has the formula R$^1$Si(OR$^3$)$_3$ and the Grignard reagent has the formula R$^2$MgX, and one of R$^1$ and R$^2$ is

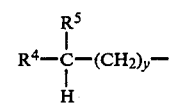

and the other is n-alkyl having 3 to 10 carbon atoms or is

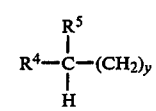

R$^4$ is alkyl having 1 to 7 carbon atoms,
R$^5$ is alkyl having 1 to 7 carbon atoms, or
R$^4$ and R$^5$ taken together with the carbon atom to which they are attached form a cycloalkyl group having 3 to 10 carbon atoms,
each R$^3$ may be the same or different and is alkyl having 1 to 5 carbon atoms,
X is Br, Cl or I, and
y is 0 or 1,
reacting at a temperature of about 0° to about 90° C. an alkylating-effective amount of said Grignard reagent with said monoorganotrialkoxysilane and thereby forming a substantially pure diorganodialkoxysilane in quantitative yields.

24. The improved process of claim 23 wherein the yield is greater than 95% and purity greater than 97%.

25. The improved process according to claim 23 wherein the effective amount of Grignard reagent is present in a molar ratio of monoorganotrialkoxysilane to Grignard reagent ranging from 1:1 to 1:10.

26. The improved process according to claim 25 wherein the molar ratio ranges from 1:1 to 1:3.

27. The improved process of claim 23, wherein the reaction is conducted in methyl-tert-butylether.

28. The improved process of claim 23 which comprises quenching any excess Grignard reagent remaining after reaction with a stoichiometric amount of an alcohol $R^3OH$ thereby forming a side product $R^3OMgX$.

* * * * *